United States Patent [19]

Turgeon

[11] Patent Number: 5,541,165
[45] Date of Patent: Jul. 30, 1996

[54] SALIVA SUBSTITUTE

[76] Inventor: Jean A. Turgeon, 308 E. Main St., Grass Valley, Calif. 95945

[21] Appl. No.: 313,393

[22] Filed: Sep. 27, 1994

[51] Int. Cl.$^6$ ..................................... A61K 31/70
[52] U.S. Cl. .................. 514/54.000; 424/49; 514/901
[58] Field of Search .................. 514/54, 901; 536/114; 424/49

[56] References Cited

U.S. PATENT DOCUMENTS

| | | | |
|---|---|---|---|
| 3,767,789 | 10/1973 | Rankin | 424/78 |
| 4,537,689 | 8/1985 | Morrow et al. | 252/11 |
| 4,879,281 | 11/1989 | Shibaski et al. | 514/55 |
| 4,887,620 | 12/1989 | Summers | 131/369 |
| 5,023,245 | 6/1991 | Kuhrts | 514/54 |
| 5,260,282 | 11/1993 | Attström et al. | 514/54 |
| 5,409,691 | 4/1995 | Swain | 424/49 |

OTHER PUBLICATIONS

*Martindale, The Extra Pharmacopoeia*, 29th Edition, Reynolds, ed., 1989, pp. 1128–1130.
*The Merck Index of Chemicals and Drugs*, 7th Edition, Stecher, ed., 1960, pp. 489–490.

*Primary Examiner*—Elli Peselev
*Attorney, Agent, or Firm*—Richard C. Litman

[57] ABSTRACT

A saliva substitute composition includes glycerin, gum, water, and a pH buffering system. Sweeteners, colorants, and preservatives may be optionally combined. The glycerin component serves both as a lubricant and as a delivery vehicle for water from the composition to moisten the mouth. The gum component provides further lubrication and serves a water retention function. Gum arabic, xanthum, or sorghum are examples. The pH buffering system includes acidic and basic components. Citric acid or citrate salts and carbonate was found to be an effective buffering system. The composition is used to maintain moisture in the mouth when little or no natural saliva is produced, providing relief from dry mouth, as a symptom of xerostomia, mucositis, and stomatitis, as well as general inflammation and/or ulceration of mucous membranes, while avoiding pH imbalances which may lead to tooth decay and/or injury to the upper digestive tract including the oral cavity, oropharynx, or esophagus. These compositions may be further incorporated in mouthwashes and soft drinks, as well as oral medicaments.

17 Claims, No Drawings

SALIVA SUBSTITUTE

BACKGROUND OF THE INVENTION

1. Field of the Invention

The present invention relates to oral compositions. More particularly, the present invention relates to oral compositions which provide substitutes for, or augmentation of natural saliva.

2. Description of the Prior Art

For millions of Americans dry mouth is a chronic disorder which may lead to numerous health, nutritional, and social hazards. Sores often develop in dry areas inside the mouth of those afflicted. Speech may become strained and painful, which may lead sufferers to withdrawal from social contact. Even eating, drinking, and breathing become difficult tasks. The inability to enjoy a standard of living taken for granted by most may further cause disillusionment and depression.

In the article "When the mouth runs dry" *Tufts University Diet & Nutrition Letter*, April 1991, Vol. 9, No. 2, pp. 7–8, it was disclosed that, over the course of several days, a group of senior citizens with dry mouth were eating foods lower in 12 nutrients ranging from vitamin A to thiamin than a group without the problem. Particularly lacking in their diets were potassium, vitamin B6, iron, calcium, and zinc as well as fiber. A reason suggested by this reference for less healthful eating is that the parched, crusty, and sensitive conditions dry mouth creates can hamper the ability to tolerate spicy or acidic foods.

Other foods, such as breads, cereals, and some fruits and vegetables, can also be difficult to chew and swallow because of a lack of saliva to moisten them. It was also found that people with dry mouth often perceive the taste and quality of their food to be poor in general, and that curbs their appetite and blunts overall interest in eating.

An even more acute problem is that serious dry mouth may make it very difficult to consume fluids. Water itself may become painful to swallow in sufficient quantity to avoid rapid dehydration. Xerostomia, the chronic condition of dry mouth, accordingly feeds on itself, leading to progressively more serious health hazards.

Atkinson, et al in "Salivary gland dysfunction: causes, symptoms, treatment," *Journal of the American Dental Association*, April 1994, Vol. 125, No.4, pp. 409–416, disclose that salivary gland dysfunction can also contribute to tooth decay, even in patients with good oral hygiene. Saliva protects teeth from acidic foods and also contains antibodies and other substances that protect against disease-causing organisms.

Yet another complication which arises from lack of natural saliva is a shift in systemic pH balance beyond the oral cavity. Korsten, et al. report in "Chronic xerostomia increases esophageal acid exposure and is associated with esophageal injury.", *American Journal of Medicine*, June 1991 Vol. 90, No. 6, pp. 701–706, that the esophagus, the connection between the pharynx and stomach, is sensitive to acids produced in the stomach. The acids can cause esophagitis when the acids are not cleared promptly.

Esophageal acid is cleared by swallowing and saliva. Reported results from monitoring the acidity of the esophagus revealed significant abnormalities in xerostomic subjects. Esophageal acid clearance was clearly delayed when saliva production was artificially inhibited by atropine or when saliva delivery into the esophagus was abolished by aspiration. It was found that patients with xerostomia accordingly had delayed esophageal acid clearance and abnormal 24-hour esophageal pH and were likely to have histologic and clinical evidence of esophagitis, which can lead to esophageal injury.

There are numerous factors which can lead to chronic dry mouth. In xerostomic individuals, saliva production is sharply or completely curtailed. Medications with anticholinergic activity can reduce salivary gland function. These include prescription drugs such as antidepressants and antipsychotics, and common over the counter drugs such as antihistamines. Xerostomia is a potential side effect of more than 250 drugs, including PROZAC, XANAX, DYAZIDE, ACTIFED, and ibuprofen as found in ADVIL, MOTRIN and NUPRIN.

Radiation treatments, microbial infections, and Sjogren's syndrome are other major causes of salivary gland dysfunction. Radiation therapy for mouth and throat cancers can destroy salivary function completely. Often, there is little choice but to undergo treatment which sacrifices normal salivary gland function. There is no known cure for radiation induced xerostomia. Accordingly, patients which undergo radiation therapy of the head, neck, and/or upper chest to enhance survival from serious maladies such as cancer usually suffer xerostomia as a condition of living.

Treatments for salivary gland dysfunction have met with limited success in the prior art. Indications may include use of artificial saliva or saliva-stimulating agents, although neither had been found to be universally effective. Artificial saliva products, which may provide temporary relief, are available under the trade names XERO-LUBE, OREX, SAL-ESE, SALIVART, and MOI-STIR. These products typically are compositions of carboxymethylcellulose and mineral salts. Other treatments often include contradictory recommendations such as: 1) eating foods with strong tastes, 2) avoiding spicy foods, 3) lubricating the mouth with a layer of oils, petroleum jelly, or butter, and 4) keeping the mouth thoroughly clean with vigilant brushing and rinsing.

Artificial saliva compositions have also been the subject of earlier patents. For example, artificial saliva compositions using a polysaccharide base are disclosed in U.S. Pat. No. 5,260,282 to Attström et al. Another artificial saliva composition, based on chitins and/or chitosans, is disclosed by U.S. Pat. No. 4,879,281 to Shibasaki et al. U.S. Pat. No. 3,767,789 to Rankin discloses a synthetic mucus composition which forms in vivo when a polyalkylene oxide solution is applied thereto.

Glycerin is of course a well known compound which has been used orally. "When your mouth goes dry," *Consumer Reports Health Letter*, August 1990, Vol. 2, No. 8, pp. 61–62, discloses that glycerine may be added to warm water to provide an oral lubricant. A composition for oral use which includes various flavors and preservatives is disclosed by U.S. Pat. No. 4,887,620 to Summers. This composition may be encapsulated in a glycerin containing gel.

Various conventional oral uses for glycerin are discussed by *Martindale, The Extra Pharmacopoeia*, 29th Edition, Reynolds, ed., 1989, pp. 1128–1130; and *The Merck Index of Chemicals and Drugs*, 7th Edition, Stecher, ed., 1960, pp. 489–490. These include the use of glycerin for reducing intra-ocular and intra-cranial pressure, as well as a lubricant, emollient, and sweetener for other drugs such as expectorants. The Martindale reference cautions that glycerin (or glycerol) may cause dehydration.

None of the above disclosures or patents, taken either singly or in combination, is seen to describe the instant invention as claimed.

SUMMARY OF THE INVENTION

The present invention relates to compositions which provides the mouth with a saliva substitute. The present compositions are effective in maintaining moisture in the mouth when little or no natural saliva is produced. The combination of glycerin with gum replicates in the mouth the texture and consistency of natural saliva. Further, the mouth is moistened by retaining and slowly delivering the water thereto.

The present compositions include glycerin, water, and a carrier having a gum component and a pH buffering system. Optionally, sweeteners, colorants, and preservatives may be combined therewith. The pH buffering system may include a combination of various mild acids or acid salts, and carbonates (basic).

The composition advantageously is taken in high dilution. The high percentage of water used in formulations of the present invention insures that dehydration and resultant exacerbation of the xerostomic condition are avoided. Upon administration, the composition may be worked into the mouth by pressing it against the fleshy walls of the oral cavity.

The composition provides relief from dry mouth, as a symptom of xerostomia, mucositis, and stomatitis, as well as general inflammation and/or ulceration of mucous membranes. The compositions of the present invention may be safely swallowed to provide further relief to the upper digestive track, including the esophagus.

All the ingredients of the present compositions are known to be safe individually. Their combination according to the present invention does not produce any new toxicities and may be used regularly, with each dose sufficient for several hours of relief from dry mouth.

Further, due to the use of a buffering system, the present composition avoids objection voiced in the prior art over pH imbalances which may lead to tooth decay and/or injury to the upper digestive tract including the oral cavity, oropharynx, or esophagus. The present compositions may be additionally incorporated in any appropriate vehicle to produce mouthwashes and soft drinks, as well as oral medicaments.

Accordingly, it is a principal object of the invention to provide artificial saliva compositions which provide relief from dry mouth.

It is another object of the invention to provide such a composition which upon administration provides a texture and consistency simulative of natural saliva.

It is a further object of the invention to provide a composition which allows delivery of sufficient water to avoid dehydration in xerostomic subjects.

It is yet a further object of the invention to provide a composition which has pH buffering to compensate for lack of natural saliva for such function.

Still another object of the invention is to provide a method for relieving dry mouth from xerostomia, mucositis, and stomatitis, as well as general inflammation and/or ulceration of mucous membranes with the compositions of the present invention.

It is an object of the invention to provide improved components and compositions thereof for the purposes described which are inexpensive, safe and fully efficacious in accomplishing its intended purposes.

These and other objects of the present invention will become readily apparent upon further review of the following description.

DETAILED DESCRIPTION OF THE PREFERRED EMBODIMENT

The present invention provides compositions for providing a saliva substitute. The compositions includes glycerin, water, and a carrier which has at least one gum component and a pH buffering system in aqueous solution.

Glycerin provides lubrication and a delivery vehicle for water from the composition to moisten the mouth. It further allows greater quantities of water to be swallowed by xerostomic subjects without discomfort. The gum component provides further lubrication and water retention. When the present compositions are orally taken and worked in the mouth, a protective mucous layer is formed which is simulative in texture and consistency to natural saliva. It should be noted that the composition itself is not necessarily gelatinous, or thickened, but forms the protective layer in the environment of the mouth.

The composition further includes a pH buffering system having acidic and basic components. Useful acidic components include: citric acid, maleic acid, and stearic acid, and salts thereof. Along with these, a basic component such as a carbonate was found to be an effective buffering system. Preferred examples of gums which may be used include at least one of gum arabic, xanthum gum, gum tragacanth, acacia, or sorghum. Most preferably gum arabic is used.

Preferably, about 5–45 ml of glycerin are combined with about ½ to 1½ liters of water, and ½ to 1½ liters of a carrier containing gum and the pH buffering system. More preferably, 15–25 ml of glycerin are dissolved in about one liter of purified water and about one liter of an aqueous carrier containing gum arabic, citric acid, and citrate. The order of combination was not seen to materially effect the composition.

Conventional flavorants, colorants, and preservatives may also be included in the composition, as desired. The aqueous carrier may be advantageously obtained with gum arabic, citric acid, sodium citrate, flavorants, colorants, and preservatives already solubilized from numerous sources. Preferably, soft drink formulations are useful as the aqueous carrier. Most preferably, conventional root beer formulations are used, wherein the formulation is allowed to acquire neutral pH by ambient exposure, i.e. allowed to go flat. The compositions of the present invention are completely safe for consumption, and may be further incorporated in mouthwashes and soft drinks, as well as oral medicaments. Additional active ingredients and carriers for mouthwashes and medicaments as conventionally used are advantageously combined with the present compositions to provide products which are easier for xerostomia sufferers to tolerate without irritation.

Preferably, the compositions are used as fluid refreshment with one modification. After imbibing and before swallowing, the compositions are worked within the mouth. Swirling the tongue and pressing the composition against the fleshy walls of the oral cavity allows a saliva substitute to form thereon. The remaining composition is swallowed with greater ease once the saliva substitute is lined within the mouth.

The compositions may be taken as needed to relieve the symptoms of dry mouth, and as fluid replenishment for those who have difficulty swallowing liquids due to dry mouth. All necessary fluid intake may be safely delivered with the present compositions. Preferably, up to 5 liters may be used and consumed. An average daily consumption of 1–3 liters is most preferred, with some deviation depending upon levels of physical exertion, external temperature, and conversation. For example when external temperatures are high, dehydration is of greater concern, and the daily quantity of the present compositions may be increased. Likewise, if consistent conversation is anticipated, more of the composition may be used. Hourly rates of up to 300 ml may be used when necessary.

EXAMPLE 1

1 liter of A&W root beer, containing: water, corn sweetener, caramel color, flavorants, sodium benzoate (preservative) propylene glycol, gum arabic, citric acid, sodium bicarbonate and sodium citrate; was allowed to acquire room temperature and neutral pH, then diluted with 1 liter of distilled water. To this 20 ml of glycerin was added. The composition was well stirred and stored at room temperature.

EXAMPLE 2

The above composition was orally taken by a xerostomic individual, worked in the mouth, then swallowed in an average quantity of 2 liters per day, on demand, over several months. The maximum dose taken per hour in that time was about 240 ml. Dry mouth was relieved upon administration, and fluid intake was substantially improved. Under full medical supervision and examination, no side effects where noted.

It is to be understood that the present invention is not limited to the embodiments described above, but encompasses any and all embodiments within the scope of the following claims.

I claim:

1. An oral composition for the relief of dry mouth and for preventing dehydration in sufferers of dry mouth, which forms a saliva substitute in the mouth, said oral composition comprising: glycerin, water, a pH buffering system, gum, and a pharmacologically acceptable carrier; wherein the percentage by volume of said glycerin is from about 0.16% to about 4.5%, the percentage by volume of water from about 25% to about 75%, and the remainder consisting essentially of said gum and pH buffering system in a pharmaceutically acceptable carrier provided in from about 25% to 75% by volume.

2. The oral composition according to claim 1, wherein said pH buffering system has an acid component and a basic component; said acid component is selected from the group consisting of citric acid, maleic acid, stearic acid and salts thereof; and said basic component is a carbonate.

3. The oral composition according to claim 2, wherein said acid component is a mixture of citric acid and sodium citrate.

4. The oral composition according to claim 1, wherein said gum is selected from the group consisting of gum arabic, xanthum gum, gum tragacanth, acacia, and sorghum.

5. The oral composition according to claim 4, wherein said gum is gum arabic.

6. The oral composition according to claim 1 which is in the form of a member selected from the group consisting of soft drinks, medicaments, and mouthwashes.

7. The oral composition according to claim 1 in which the percentage by volume of glycerin is from about 0.25% to about 2.25%.

8. The oral composition according to claim 7 in which the percentage by volume of glycerin is about 1.00%.

9. A method for alleviating the symptoms of dry mouth by providing a saliva substitute in the mouth, in subjects in need thereof comprising:

a) orally administering a composition according to claim 1; and b) working said composition within the mouth to form said saliva substitute.

10. The method according to claim 9, further comprising the subsequent step:

c) swallowing said composition; whereby dehydration is substantially prevented.

11. The method according to claim 10, wherein said pH buffering system of said composition has an acid component and a basic component; said acid component selected from the group consisting of citric acid, maleic acid, stearic acid and salts thereof; and said basic component is a carbonate.

12. The method according to claim 11, wherein said acid component is a mixture of citric acid and sodium citrate.

13. The method according to claim 10, wherein said gum of said composition is selected from the group consisting of gum arabic, xanthum gum, gum tragacanth, acacia, and sorghum.

14. The method according to claim 10, wherein said gum of said composition is gum arabic.

15. The method according to claim 9, wherein said composition is in the form of a member selected from the group consisting of soft drinks, medicaments, and mouthwashes.

16. The method according to claim 9, in which the percentage by volume of glycerin in said composition is from about 0.25% to about 2.25%.

17. The method according to claim 9, in which the percentage by volume of glycerin in said composition is about 1.00%.

* * * * *